United States Patent [19]

Dalton

[11] Patent Number: 5,315,992
[45] Date of Patent: May 31, 1994

[54] TRIPLE CUFF ENDOBRONCHIAL TUBE WITH SELECTIVE MULTIPLE OUTLETS SERVED BY A SINGLE AIRFLOW PASSAGE

[76] Inventor: William J. Dalton, 7865 Ivygate La., Cincinnati, Ohio 45242

[21] Appl. No.: 29,117

[22] Filed: Mar. 10, 1993

[51] Int. Cl.$^5$ .................... A61M 16/00; A61M 25/00
[52] U.S. Cl. ........................ 128/207.15; 128/207.14; 604/43; 604/101
[58] Field of Search ............... 128/207.14, 207.15, 128/200.24, 202.28; 604/43, 95–103

[56] References Cited

U.S. PATENT DOCUMENTS

| | | | |
|---|---|---|---|
| 4,248,221 | 2/1981 | Winnard | 128/207.15 |
| 4,351,330 | 9/1982 | Scarberry | 128/207.15 |
| 4,423,725 | 1/1984 | Baran | 128/207.15 |
| 4,453,545 | 6/1984 | Inoue | 128/207.15 |
| 4,584,998 | 4/1986 | McGrail | 128/207.15 |
| 4,688,568 | 8/1987 | Frass | 128/207.15 |
| 4,751,924 | 6/1988 | Hammerschmidt | 128/207.15 |
| 4,819,664 | 4/1989 | Nazari | 128/207.15 |
| 4,976,261 | 12/1990 | Gluck | 128/207.15 |
| 5,065,755 | 11/1991 | Klafta | 128/200.26 |

FOREIGN PATENT DOCUMENTS 1289503 2/1987 U.S.S.R. .................... 128/207.15

Primary Examiner—Edgar S. Burr
Assistant Examiner—Eric P. Raciti
Attorney, Agent, or Firm—Wood, Herron & Evans

[57] ABSTRACT

An endobronchial tube with a single lumen air flow passage is disclosed. The endobronchial tube includes three balloon cuffs, two longitudinally spaced to engage the trachea and one positioned within the bronchus of the patient, and dual air outlet ports. One of the air outlet ports is positioned between the two balloon cuffs within the trachea of the patient and the other air outlet port is positioned at a distal end of the tube, so that it will exit to the bronchus in use. The tube affords the capability of selectively ventilating one or both lungs of the patient after intubation, by inflating one or more of the cuffs. Additionally, this capability is provided with a single larger diameter air passage lumen than is available from double lumen endobronchial tubes of the prior art. The larger single lumen offers the capability of inserting auxiliary monitoring, diagnostic, and treatment instrumentation through the tube, a capability which is restricted with the smaller diameter double lumen endobronchial tube.

7 Claims, 1 Drawing Sheet

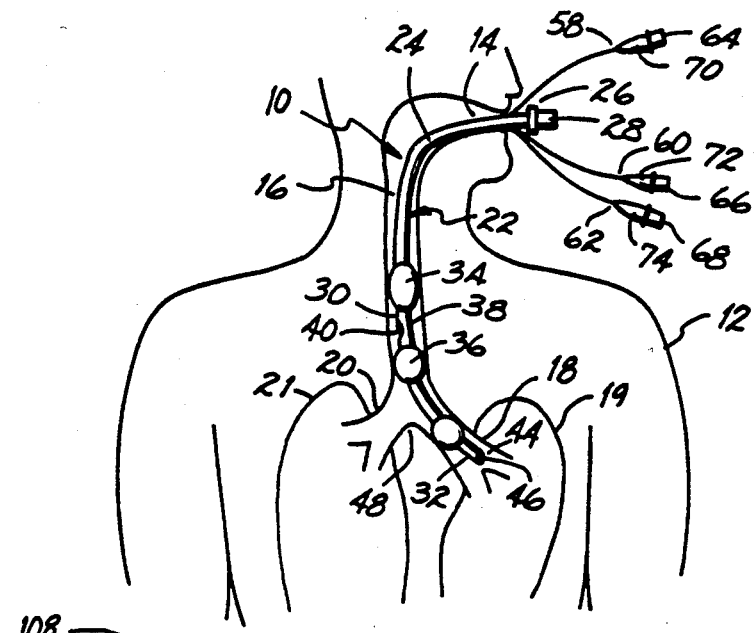
FIG. 1
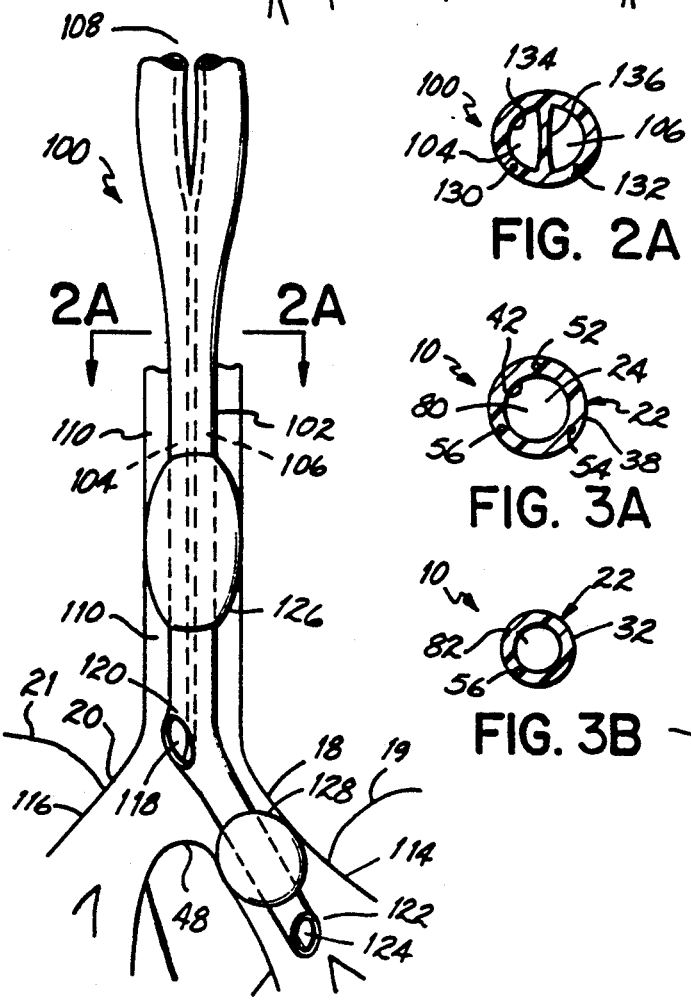
PRIOR ART
FIG. 2
FIG. 2A
FIG. 3A
FIG. 3B
FIG. 3

TRIPLE CUFF ENDOBRONCHIAL TUBE WITH SELECTIVE MULTIPLE OUTLETS SERVED BY A SINGLE AIRFLOW PASSAGE

BACKGROUND OF THE INVENTION

This invention relates generally to endobronchial tubes for insertion through the mouth or nasal passages of a patient to facilitate artificial ventilation of the respiratory system. More particularly, this invention relates to endobronchial tubes with a single primary bore or lumen and multiple balloon cuffs for selective ventilation of one or both lungs.

It is a common practice to provide human medical patients with artificial ventilation during surgery or in emergency situations. For example, accident victims will frequently require CPR or intubation by a paramedic in an emergency vehicle or by an anesthesiologist in an operating room. In such situations, intubation is accomplished by insertion of an endotracheal tube through the patient's mouth or nasal passages into the airway passage. Such devices have generally comprised a relatively pliable tube with means for connecting it to a respirator or other air supply mechanism for introduction of air into the lungs. An improvement to endotracheal tubes includes an inflatable-deflatable bag-like structure or balloon "cuff" around the exterior of the tube. The balloon cuff is conventionally located in a position along the endotracheal tube to engage the inner wall of the pharynx, larynx, or trachea depending upon the specific endotracheal tube design. When the tube is in place, the cuff is inflated and forms an air tight seal between the tube and the surrounding body tissue to prevent the escape of air pumped from the respirator into the lungs.

Both single lumen and double lumen endotracheal tubes are known. Typically, a single lumen endotracheal tube is an elongated tube that extends into the trachea of a patient upon intubation and includes one inflatable balloon cuff near its distal end. Commonly, the double lumen endotracheal tube is referred to as an endobronchial tube and, in addition to one lumen which extends to the trachea, has a second longer lumen which extends into the bronchus of a patient upon intubation. Typically, the double lumen endotracheal tube or endobronchial tube includes two inflatable balloon cuffs. The so-called double lumen endobronchial tubes, such as the well known "Carlens" and "Robertshaw" tubes, allow for independent control of each lung through the separate lumina. One bronchus may be blocked by occluding one of the lumina at a position external to the patient, in order to isolate a particular lung.

The balloon cuffs are thin walled, high volume, and low pressure chambers or vessels which are designed not to compromise the blood flow in the tracheal or bronchial wall when inflated. Balloon cuffs are inflated by detachable syringes that are connected to smaller lumina or channels at the proximal end of the endotracheal tube. The seals formed by the inflated cuffs preclude the air that has been forced into the patient's lungs from escaping through the trachea or bronchus. Additionally, the seals formed by the inflated cuffs provide a barrier to the flow of blood and secretions.

The so-called double lumen endobronchial tubes offer the anesthesiologist the ability to insufflate selectively either the right or left lung or both lungs as required. However, in order to minimize damage to the tissue on the tracheal wall, the overall outer diameter of both single and double lumen endobronchial tubes is limited to approximately 1.2 cm. For this reason, the inner diameter of each lumen of a double lumen endobronchial tube is by necessity smaller than the inner diameter of a single lumen endotracheal tube. As a result, the inner diameter of the single lumen endotracheal tube can typically be no more than about 7.5 mm; whereas, the inner diameter of each lumen in a double lumen endobronchial tube is limited to a maximum of approximately 3.5 mm.

Another endobronchial tube design which offers the anesthesiologist the capability to insufflate one or both lungs of a patient is shown in U.S. Pat. No. 4,248,221. The endobronchial tube disclosed in that patent includes a single lumen with three balloon cuffs. Two of the cuffs are located on the outer surface of the tube and the third is located within the lumen between two outlet ports in the tube. By positioning the tube of U.S. Pat. No. 4,248,221 in the trachea and one mainstem bronchus of the patient and selectively inflating the individual balloon cuffs, one or both of the patient's lungs may be insufflated. However, in that one of the balloon cuffs is internal to the lumen, access through the lumen is blocked.

The larger lumen provided in a single lumen endotracheal tube having no internal lumen balloon cuffs affords the anesthesiologist access for other instrumentation through the lumen as required. The removal of mucous, the injection of medication, or the insertion of fiber optic instrumentation for viewing within the endotracheal tube are examples of the additional instrumentation capability which is afforded by a single lumen tube. The ability to insert fiber optic instrumentation through the tube significantly aids the anesthesiologist during intubation to accurately determine if the endobronchial tube is correctly positioned within the trachea and bronchus of the patient. These capabilities are restricted, if not prohibited, in the double lumen endobronchial tubes which by necessity have more narrow inner diameter passages and afford less access through the tubes by the anesthesiologist for the probes and instrumentation described.

Although the use of various double cuff arrangements with double lumen endobronchial tubes offer advantages which are not present in single lumen endotracheal tubes, namely the capability to insufflate one or both lungs from a single tube, these advantages cannot be provided with currently available single lumen tubes. However, the use of single lumen tubes offers the advantages of additional instrumentation capability through the larger lumen tube which cannot be provided with current double lumen tubes. For these and other reasons both prior art single and double lumen tubes are not fully satisfactory.

SUMMARY OF THE INVENTION

It has been an objective of the present invention to provide an endobronchial tube which allows access through a single lumen for auxiliary instrumentation while maintaining the capability of selectively insufflating one or both of the patient's lungs. The access is beneficial to allow the anesthesiologist sufficient space through the tube for instrumentation to monitor the positioning of the tube and the patient's condition.

This objective of the present invention is provided by a single lumen endobronchial tube with three longitudinally spaced balloon cuffs and two outlet ports positioned along the length of the tube.

The present invention is directed to an endobronchial tube which can be inserted through the mouth and past the larynx of a patient and into the tracheal and mainstem bronchial passages. Extending from the tracheal portion of the tube is a bronchial portion which may be placed in either the left or right mainstem bronchi of the patient. The single lumen of the endobronchial tube of the present invention may have an inner diameter of approximately 7.5 mm, and thus offers sufficient space for the anesthesiologist to access through the single lumen the patient's lungs and respiratory system with additional instrumentation, as required.

Positioned along the tracheal portion of the endobronchial tube of the present invention are two longitudinally spaced balloon cuffs which can be selectively inflated and deflated. When inflated, the tracheal balloon cuffs prevent retrograde air from escaping between the endobronchial tube and the trachea. Positioned between the two tracheal balloon cuffs is an air outlet port from the tube through which oxygen from a respirator input to the endobronchial tube can escape into the patient's respiratory system in order to ventilate the lungs.

Located at a distal end of the bronchial portion of the endobronchial tube is a second air outlet port through which air (or oxygen) input to the tube through a respirator can exit to ventilate a particular lung attached to the mainstem bronchus in which the bronchial portion is located. A third balloon cuff is provided around the bronchial portion of the endobronchial tube between the distal end of the bronchial portion and the tracheal portion of the tube. The bronchial balloon cuff when inflated serves to block retrograde air from escaping between the bronchial walls and the bronchial portion of the tube of the present invention.

Each of the balloon cuffs of the present invention can be selectively inflated or deflated through secondary lumina which are preferably provided within the walls of the primary lumen of the endobronchial tube. These secondary lumina do not diminish the inner diameter of the primary lumen in that they are located within the endobronchial tube wall. The conventional endobronchial tube wall is of sufficient thickness to accommodate the secondary lumina without increasing the wall thickness nor altering the spatial dimensions of the single primary lumen endobronchial tube. A distal end of each secondary lumen has an opening leading to the respective balloon cuff. Attached to a proximal end of each secondary lumen is a connector located external to the patient, to which the anesthesiologist or care provider may connect a syringe or other suitable apparatus for selectively inflating the balloon cuff. (Connectors of this type are known in the industry, and operate to block the escape of air or fluid from the inflated balloon cuff or to inhibit the introduction of air into the deflated balloon cuff as required.)

BRIEF DESCRIPTION OF THE DRAWINGS

The objectives and features of the invention will become more readily apparent from the following detailed description taken in conjunction with the accompanying drawings in which:

FIG. 1 is a diagrammatic view of an endobronchial tube of the present invention, as inserted into a patient's tracheal and bronchial passages;

FIG. 2 is a partial sectional view of a prior art double lumen endobronchial tube inserted into the tracheal and bronchial passages;

FIG. 2A is an enlarged cross-sectional view taken along line 2A—2A of FIG. 2 showing the reduced inner diameters of each lumen of the prior art endobronchial tube;

FIG. 3 is an enlarged diagrammatic view of an endobronchial tube of the present invention inserted into the tracheal and bronchial passages showing in detail the positioning of the tube within the patient and the spatial relationships of the dual ports and triple balloon cuffs;

FIG. 3A is an enlarged cross-sectional view of the single primary lumen taken along line 3A—3A of FIG. 3; and FIG. 3B is an enlarged cross-sectional view of the bronchial portion of the tube of the present invention, taken along line 3B—3B of FIG. 3.

DETAILED DESCRIPTION OF THE PRESENT INVENTION

Referring to FIG. 1, an endobronchial tube 10 according to the present invention is shown as positioned within a patient 12. The endobronchial tube 10 has been inserted through a mouth 14 of the patient 12 and into a trachea 16 and left mainstem bronchi 18 of the patient 12. The figures and accompanying detailed description herein will focus on the endobronchial tube 10 being inserted through the trachea 16 and into the patient's left mainstem bronchi 18 in that according to the geometry of the human respiratory system, typically the patient's left mainstem bronchi 18 affords easier intubation. However, as required depending on the treatment demands of a specific medical situation, the endobronchial tube 10 of the present invention can also be used for intubation into a right mainstem bronchi 20 of the patient.

The endobronchial tube 10 of the present invention comprises a main tube 22 having a primary air flow passage or lumen 24 passing therethrough. Attached to a proximal end 26 of the tube 22, located external to the mouth 14 of the patient 12, is a respiratory connector 28, which may be of a type known per se.

The tube 22 of the present invention includes a tracheal portion 30 which upon intubation is located within the trachea 16 of the patient 12. Extending from the tracheal portion 30 is a bronchial portion 32 which upon intubation is positioned within one of the mainstem bronchi 18, 20 of the patient. As shown in FIG. 1, the bronchial portion 32 is located in the patient's left mainstem bronchi 18; however, as previously described the present invention is also functional for intubation into the right mainstem bronchi 20. With the bronchial portion 32 extending into the patient's left mainstem bronchi 18, the endobronchial tube 10 can be used to insufflate a left lung 19 of the patient or both lungs of the patient as will be described later in this detailed description. Similarly, a right lung 21 of the patient or both lungs of the patient may be insufflated if the bronchial portion 32 is inserted into the right mainstem bronchi 20.

A first and a second sealing means or tracheal balloon cuffs 34, 36 are spaced longitudinally along an exterior surface 38 of the tube on the tracheal portion 30 as shown in FIG. 1. A first air outlet or tracheal port 40 is provided through a wall 42 of the tube 22 between the first and second tracheal balloon cuffs 34, 36 in the tracheal portion 30. Although the tracheal port 40 could functionally be any shape, in a preferred embodiment the tracheal port 40 is oval shaped and is positioned so as not to interfere with the balloon cuffs or the inflation means for the balloon cuffs as to be described later in this disclosure. Furthermore, the tracheal port 40 is obliquely angled with respect to the tube wall 42 of the trachea portion 30 in order to aid the efficient flow of air exiting through the tracheal port 40. In order to enhance the flow of air exiting from the trachea portion 30, multiple ports of various sizes and configurations could be provided in the tube wall 42 between the tracheal balloon cuffs 34, 36 according to the present invention.

Located at a distal end 44 of the bronchial portion 32 is a second air outlet or bronchial port 46 and positioned between the bronchial port 46 and a carina 48 of the patient 12, where the left and right mainstem bronchi 18, 20 diverge, is a third sealing means or bronchial balloon cuff 50 around the bronchial portion 32 of the tube 22. The bronchial port 46 in the preferred embodiment of the present invention is at an angle A with respect to a longitudinal axis L of the bronchial portion 32. The angle A is preferably within the range of approximately 30 to 60 degrees. An edge 47 of the bronchial port 46 is rounded or beveled which, in combination with the angle A, assists during intubation to avoid damage to the trachea or bronchus tissue and to minimize the likelihood of the port 46 catching or snagging on the tissue walls.

The bronchial balloon cuff 50 and the tracheal balloon cuffs 34, 36 are each remotely and selectively inflatable through pilot tubes 52, 54, 56 located within a wall of the tube as seen in FIGS. 3A and 3B. Each pilot tube 52, 54, 56 emerges from the tube wall 42 near the proximal end 26 of the tube 22 external of the patient's mouth 14 as shown in FIG. 1. Attached to a proximal end 58, 60, 62 of each pilot tube 52, 54, 56 is a non-return valve 64, 66, 68 which is adapted to receive the nozzle of a syringe (not shown), and a pilot balloon 70, 72, 74 which enables the anesthesiologist to confirm that each balloon cuff 34, 36, 50 has been inflated. The pilot tubes 52, 54, 56 and non-return valves 64, 66, 68 are standard and well known in the industry.

In contrast to the single lumen endobronchial tube 10 and triple balloon cuffs of the present invention, a prior art double lumen endobronchial tube 100 is shown in FIG. 2. The double lumen endobronchial tube 100 comprises, in part, a generally elongated tracheal portion 102 which is divided into two separate ducts, specifically, a tracheal duct 104 and a bronchial duct 106. The tracheal duct 104 and bronchial duct 106 are initially separated at a proximal end 108 of the tube 100 to form the dual duct tracheal portion 102, but then merge and extend side by side within a trachea 110 of a patient. However, as the trachea 110 diverges into a left and right mainstem bronchi 114, 116, the tracheal duct 104 terminates into a tracheal duct port 118 at a distal end 120 thereof. The bronchial duct 106 continues on past the distal end 120 of the tracheal duct 104 into the left mainstem bronchi 114 of the patient as drawn in FIG. 2. Located at a distal end 122 of the bronchial duct 106 is a bronchial port 124.

The double lumen bronchial tube 100 of the prior art shown in FIG. 2 includes a tracheal balloon cuff 126 around both the tracheal duct 104 and the bronchial duct 106 positioned in the trachea 110 of the patient and a bronchial balloon cuff 128 positioned in the mainstem bronchi 114 of the patient around the bronchial duct 106. A cross-sectional view of the double lumen endobronchial tube 100 showing the tracheal duct 104 and the bronchial duct 106 is shown in FIG. 2A. Pilot tubes 130, 132 for the selective inflating and deflating of the tracheal balloon cuff 126 and the bronchial balloon cuff 128 are also shown in a wall 134 of the endobronchial tube 100 of the prior art.

After intubation, the prior art double lumen endobronchial tube 100 is capable of ventilating the left lung, the right lung, or both lungs of the patient. In order to ventilate the patient's right lung only, a respirator (not shown) would be connected to the proximal end (not shown) of the tracheal duct 104. Both the tracheal balloon cuff 126 and the bronchial balloon cuff 128 would be inflated as shown in FIG. 2. In this way, air input through the tracheal duct 104 would be directed into the patient's right mainstem bronchi 116 for insufflation of the right lung and retrograde air flow up the patient's trachea 110 or into the patient's left mainstem bronchi 114 will be prevented as a result of the seal provided by each balloon cuff 126, 128.

Additionally, to ventilate the patient's left lung only with the prior art device of FIG. 2, the respirator would be connected to a proximal end (not shown) of the bronchial duct 106 and the bronchial balloon cuff 128 would be inflated. In this way, air input to the bronchial duct 106 would flow into the patient's left mainstem bronchi 114 to insufflate the left lung and would be prevented from retrograde movement by the seal provided in the left mainstem bronchi 114 by the bronchial balloon cuff 128. To ventilate both lungs with the prior art tube 100, air would be input to both the tracheal duct 104 and the bronchial duct 106 as previously described and both the tracheal and bronchial balloon cuffs 126, 128 would be inflated to prevent the escape of retrograde air.

As shown in FIG. 2A, the bronchial duct 106 and tracheal duct 104 of the prior art tube 100 are divided by a separation wall 136 within the double lumen endobronchial tube 100. As a result, each duct of the prior art endobronchial tube is of a smaller internal diameter than the single lumen endobronchial tube 10 of the present invention as shown in FIG. 3A. The reduced inner diameter of each duct 106 or 104 relative to the single lumen 24 of the present invention serves to restrict, if not preclude, access through either duct 106 or 104 for auxiliary instrumentation. Unlike the prior art double lumen tube 100 of FIG. 2, this capability is available in the endobronchial tube 10 of the present invention as shown in FIGS. 1 and 3.

The intubation configuration for the endobronchial tube 10 of the present invention which will be used for ventilation of the patient's left lung is shown in FIG. 3. In operation, the single lumen endobronchial tube 10 of the present invention, after intubation and connection to a respirator (not shown), can be used to insufflate the patient's left lung 19 if inserted into the left mainstem bronchi 18, the patient's right lung 21 if inserted into the right mainstem bronchi 20, or both lungs 19, 21 regardless of which mainstem bronchi is used. To ventilate the left lung 19 solely, both tracheal balloon cuffs 34, 36 and the bronchial balloon cuff 50 would be inflated to provide a seal between the tube 22 and the adjoining tracheal and bronchial walls, respectively. Air supplied from the respirator would exit both the tracheal port 40 and bronchial port 46 of the present invention. However, with both tracheal balloon cuffs 34, 36 inflated, once a region 76 in the trachea 16 between the tracheal balloon cuffs 34, 36 is filled with air, the air supplied by the respirator would be inhibited from exiting the tracheal port 40 and continue through the tracheal and bronchial portions 30, 32 of the tube 22 and exit the bronchial port 46, thereby ventilating the left lung 19. In order to ventilate solely the right lung 21, the same procedure as previously described would be employed after intubation of the bronchial portion 32 into the right mainstem bronchi 20 of the patient 12.

In order to insufflate both lungs 19, 21 with the single lumen endobronchial tube 10 of the present invention, the bronchial portion 32 will be positioned in either mainstem bronchi 18, 20 and the first tracheal balloon cuff 34 along with the bronchial balloon cuff 50 would be inflated. For example, as shown in FIG. 3, the second tracheal balloon cuff 36 would be deflated by release of air pressure contained therein resulting in the deflated configuration as shown by phantom lines 78. Therefore, air supplied from the ventilator would exit the tracheal port 40 to insufflate the right lung 21, whereas air from the ventilator which bypasses the tracheal port 40 would exit the bronchial port 46 thereby insufflating the left lung 19. In order to accommodate the reduced dimension of the mainstem bronchi 18, 20 relative to the trachea 16, the bronchial portion 32 is of a slightly reduced diameter 82 than tracheal portion 30 as seen by comparing FIGS. 3A and 3B. In the preferred embodiment of the present invention, the bronchial portion 32 is approximately 8.0 to 9.0 mm outer diameter as in FIG. 3B; whereas the outer diameter of the tracheal portion 30 of FIG. 3A is approximately 10.0 to 12.0 mm.

The advantage afforded by the present invention single lumen endobronchial tube 10 over prior art double lumen endobronchial tubes 100 is that the tracheal portion 30 of the tube 22 can be of substantially larger inner diameter 80 than that which is possible with the tracheal duct 104 or the bronchial duct 106 of prior art tubes. In a preferred embodiment of the present invention, the inner diameter 80 of the tracheal portion is approximately 6.5 to 7.5 mm. The larger inner diameter of the single tube 22 of the present invention relative to the smaller inner diameters of either duct 104, 106 in the prior art tubes affords the anesthesiologist the use of auxiliary instrumentation such as fiber optic apparatus, medication delivery tubes, and mucous removal tools, within the tube 22. Moreover, the greater available space within the single lumen of the present invention provides for the relatively easy removal of mucous, insertion of fiber optic instrumentation, or other required medical equipment for monitoring or administering the ventilation of the patient's lungs. This added capability of access within the single lumen within the bronchial tube is available without sacrificing the capability of selectively ventilating either or both lungs of the patient.

From the above disclosure of the general principles of the present invention and the preceding description of the preferred embodiment, those skilled in the art will readily comprehend the various modifications to which the present invention is susceptible. Therefore, I desire to be limited only by the scope of the following claims.

Having described the invention, what is claimed is:

1. An endobronchial tube for selectively delivering air to one or both lungs of a human patient comprising:

a tube with a longitudinal air flow passage for supplying air to ventilate at least one lung of a patient, said air flow passage extending the length of said tube, said tube having a tracheal portion adapted to be positioned within the trachea of a patient, said tube also having a bronchial portion extending from said tracheal portion and adapted to be positioned within one of the bronchi of a patient when said tracheal portion is positioned within the trachea;

selectively inflatable longitudinally spaced first and second sealing means around said tracheal portion for selectively blocking air from flowing between said tracheal portion of said tube and the trachea; said passage having a first air outlet port, said first outlet port being located in said tracheal portion between said first and second sealing means, said first port providing an outlet for air from said said passage also having a second air outlet port, said second outlet port being located adjacent a distal end of said bronchial portion, said second port providing an outlet for air from said passage; and third sealing means around said bronchial portion between said second sealing means and said second port for selectively blocking air from flowing between said bronchial portion and the bronchus, said third sealing means being so spaced axially on said tube from said second sealing means that in use said third sealing means is positioned in the bronchus and said second sealing means is positioned in the trachea.

2. The endobronchial tube of claim 1 wherein said first, second, and third sealing means comprise selectively inflatable first, second, and third balloon cuffs affixed around an outer surface of said tube, and air supply means for selectively individually inflating said first, second, and third cuffs.

3. The endobronchial tube of claim 2 wherein said air supply means comprises a lumen extending longitudinally within a sidewall of said tube from each said cuff to a connector located external to the patient, said connector adapted for both delivery of air through said lumen to said cuff and blockage of air from escaping through said lumen from said inflated cuff.

4. The endobronchial tube of claim 1 wherein said bronchial portion is of a smaller cross-sectional area than said tracheal portion.

5. The endobronchial tube of claim 1 wherein said second sealing means is so located axially on said tracheal portion of said tube that in use, said second sealing means is positioned within the trachea of a patient above the separation of the mainstem bronchi, and said third sealing means is so located along said bronchial portion of said tube that in use said third sealing means is positioned below the separation of the mainstem bronchi.

6. The endobronchial tube of claim 1 wherein said second air outlet port is angled approximately 30° to 60° with respect to a longitudinal axis of said bronchial portion to aid in the intubation of said endobronchial tube into a patient.

7. The endobronchial tube of claim 1 wherein said first air outlet port is oblong and angled obliquely with respect to a longitudinal axis of said tracheal portion to aid the escape of air from said tracheal portion.

* * * * *